United States Patent
Iwai

(10) Patent No.: US 6,387,417 B1
(45) Date of Patent: May 14, 2002

(54) BACTERICIDE AGAINST VANCOMYCIN RESISTANT ENTEROCOCCUS

(76) Inventor: Kazuo Iwai, 1221-1, Oaza Koshinohara, Yasu-cho, Yasu-gun, Shiga-ken (JP)

( * ) Notice: Subject to any disclaimer, the term of this patent is extended or adjusted under 35 U.S.C. 154(b) by 0 days.

(21) Appl. No.: 09/665,706

(22) Filed: Sep. 20, 2000

(51) Int. Cl.⁷ .............................................. A61K 35/78
(52) U.S. Cl. ................... 424/729; 424/744; 424/750; 424/405; 424/725
(58) Field of Search ................. 424/195.1, 405, 424/401, 725; 514/642, 358, 783

(56) References Cited

U.S. PATENT DOCUMENTS

| | | | |
|---|---|---|---|
| 5,525,340 A | * | 6/1996 | Fukunaga |
| 5,696,169 A | | 12/1997 | Otsu |
| 5,993,867 A | * | 11/1999 | Rohdewald |
| 6,025,312 A | * | 2/2000 | Saito et al. |
| 6,048,836 A | * | 4/2000 | Romano et al. |
| 6,183,748 B1 | * | 2/2001 | Tozaka |

FOREIGN PATENT DOCUMENTS

| | | |
|---|---|---|
| EP | 0 900 560 A1 | 3/1999 |
| EP | 0 997 520 A1 | 5/2000 |
| EP | 1 000 542 A1 | 5/2000 |
| EP | 1 026 144 A1 | 8/2000 |
| EP | 1 062 871 A1 | 12/2000 |
| WO | WO99/45784 | 9/1999 |

OTHER PUBLICATIONS

Abstract of Japanese Application No. JP11021591, 1997, Database Accession No. XP002160705, T. Ishimura, "Soaps with Good Foaming and Sterilizing, Skin–Conditioning, and Deodorant Effect" Abstract.

G. Kampf et al., "Efficacy of Hand Disinfectants against Vancomycin–Resistant Enterococci in Vitro", Journal of Hospital Infection, vol. 42, No. 2, Jun. 1999, pp. 143–150, Berlin.

Abstract of Japanese Application No. JP1040402, published on Oct. 2, 1989, Database Accession No. XP002160707, O. Yoshimitsu et al., "Natural Disinfectant and Germicide" Abstract.

Ido et al., "Induction of apoptosis be hinokitiol, a potent iron chelator, in teratocarcinoma F9 cells is mediated through the activation of caspase–3", Cell Proliferation, Feb. 1999, 32(1), p. 63–73.*

* cited by examiner

Primary Examiner—Leon B. Lankford, Jr.
Assistant Examiner—Ruth Davis
(74) Attorney, Agent, or Firm—Bacon & Thomas

(57) ABSTRACT

The present invention provides a method of sterilizing VRE using a composition which contains hinokitiol, a metal complex thereof or their salt as an effective component, and aloe extract and the like extracts as preferably used. The composition is administered to an animal infected with VRE, or a site contaminated with VRE.

10 Claims, No Drawings

BACTERICIDE AGAINST VANCOMYCIN RESISTANT ENTEROCOCCUS

BACKGROUND OF THE INVENTION

1. Field of the Invention

The present invention relates to a bactericide against vancomycin resistant Enterococcus for use in such applications as sterilization of vancomycin resistant Enterococcus (hereinafter referred to as "VRE" simply) that is resistant to vancomycin hydrochloride, disinfection of a site contaminated with VRE, and intestinal sterilization of VRE in animals (human, bovine, chicken, and the like) in which VRE is possible to grow at their intestines.

2. Description of the Related Art

The vancomycin hydrochloride exhibits bactericidal activity on most of bacteria and bacteriostatic activity on Enterococcus. The vancomycin hydrochloride is effective even against methicillin resistant *Staphylococcus aureus* (hereinafter referred to as "MRSA" simply) which has been at issue particularly recently as a bacterium causing nosocomial infection, and hence has been approved as an antibiotic against MRSA in many countries including Japan.

As the vancomycin hydrochloride has been increasingly used as a remedy for diseases caused by the MRSA, there have appeared bacteria having a resistance to the vancomycin hydrochloride. Accordingly, a substance exhibiting bactericidal or antibacterial activity on VRE has now been desired.

SUMMARY OF THE INVENTION

The inventor of the present invention has discovered a fact that hinokitiol known as a bactericidal substance having a relatively extensive antibacterial spectrum is also effective against VRE. The present invention has been attained based on this discovery.

One object of the present invention is to provide a method of sterilizing a vancomycin resistant Enterococcus. The method comprises use of a bactericide containing hinokitiol, a metal complex thereof or their salt as an effective component.

Another objection of the present invention is to provide a method comprising administering an effective amount of a composition containing hinokitiol, a metal complex thereof or their salt to an animal infected with a vancomycin resistant Enterococcus.

Another object of the present invention is to provide a method of disinfecting, the method comprising administering an effective amount of a composition containing hinokitiol, a metal complex thereof or their salt to a site contaminated with a vancomycin resistant Enterococcus.

The foregoing and other objects, features and attendant advantages of the present invention will be more fully appreciated from the reading of the following detailed description.

DESCRIPTION OF THE PREFERRED EMBODIMENTS

A composition for use of sterilizeing a vancomycin resistant Enterococcus, or a bactericide against VRE used in the present invention, contains hinokitiol, a metal complex thereof or their salt as an effective component.

One method of the present invention comprises administering an effective amount of the composition to an animal (e.g. human, bovine, chicken, and pet such as cat and dog) infected with the vancomycin resistant Enterococcus, thereby treating the animal.

Another method of the present invention comprises administering an effective amount of the composition to a site contaminated with the vancomycin resistant Enterococcus, thereby disinfecting the site.

Hereinafter, the composition (i.e. bactericide against VRE) used in the present invention is described in detail.

An effective component in the composition is Hinokitiol, which is otherwise termed β-Thujaplicin. Hinokitiol is contained in essential oils extracted from such plants as Taiwan hinoki cypress (*Chamaecyparis obtusa* var *formosana*), Aomori hiba (*Thulopsis dolabrata* var *hondai*) and a species of incense cedar (*Calocedrus decurrens*). Not only natural hinokitiol, but also synthetic hinokitiol may be used. Such natural or synthetic hinokitiol is commercially available, for example, from TAKASAGO PERFUME CO., LTD. and OSAKA ORGANIC CHEMICAL IND., LTD.

Examples of metal complexes of hinokitiol include those complexes of hinokitiol with zinc, copper, iron, calcium, magnesium, barium, tin, cobalt, titanium and vanadium. The ratio of hinokitiol to such a metal is not particularly limited, but 2:1 or 3:1 in molar ratio is generally preferable.

Examples of specific salts of hinokitiol or salts of metal complexes of hinokitiol include alkali metal salts such as sodium salts and potassium salts; alkali earth metal salts such as calcium salts and magnesium salts; transition metal salts such as copper salts and zinc salts; alkanolamine salts such as diethanolamine salts, 2-amino-2-ethyl-1,3-propanediol salts and triethanolamine salts; heterocyclic amine salts such as morpholine salts, piperazine salts and piperidine salts; and basic amine salts such as ammonium salts, arginine salts, lysine salts and histidine salts.

Hinokitiol, metal complexes thereof or their salts may be used either alone or in combination of two or more of them depending on the type of a composition to be prepared. In the case of administering the composition into a human body directly, e.g. oral administration, it is preferable to use hinokitiol as it is. On the other hand, metal complexes of hinokitiol or salts of these metal complexes have higher resistance to light than hinokitiol as it is and hence are preferable when the metal complex or the salt of hinokitiol is adapted for applications requiring resistance to light.

Hinokitiol, a metal complex thereof or their salt (hereinafter referred to as "hinokitiol or its analog" unless referred to distinctively) exhibits potent antibacterial activity on VRE. Though hinokitiol is known to exhibit wide antibacterial activity on aerobic bacteria such as tubercle bacillus and typhoid bacillus, anaerobic bacteria such as clostridium, food poisoning pathogens such as Salmonella, and other bacteria including *E. colli*, the inventor of the present invention has made the first discovery that hinokitiol possesses bactericidal activity on VRB.

When hinokitiol or its analog is used alone, hinokitiol in an amount of about 50 to about 100 μg can exhibit an effective bactericidal action against VRE.

According to the present invention, a preferable composition for the bactericide against VRE further contains at least one selected from the group consisting of respective extracts of aloe, green tea, low striped bamboo and dokudami (hereinafter referred to as "aloe extract and like extracts" unless referred to distinctively). These extracts serve to enhance the antibacterial activity against VRE of hinokitiol and hence contribute to a reduction in the amount of hinokitiol to be required to inhibit the growth of VRE. Where the bactericide is used in the form of an aqueous solution, coexistence of at least one of the aloe extract and like extracts with hinokitiol is particularly preferable. This is because the aloe extract and like extracts can readily provide for an aqueous solution of about 1% by mass hinokitiol, although the limit of the solubility of hinokitiol in water without the aloe extract and like extracts is generally 0.2% by mass.

The aloe extract is made by press extracting aloe leaves, particularly a jelly-like flesh thereof, and heating the aloe juice thus extracted for concentration and stabilization. Instead of such an aloe extract, it is possible to use aloin, which is an anthraquinone derivative forming a principal component of the aloe extract, or barbaloin. The aloe extract contains aloe-emodin, aloesin, aloenin and the like, in addition to aloin and barbaloin.

The green tea extract is a liquid prepared by extracting ground green tea with hot water, followed by purification and concentration. The main component of the green tea extract is tea polyphenol, which is a general term of compounds having a phenolic hydroxyl group in a molecule thereof and contains, as principal components, catechin, epi-catechin, gallo-catechin, epi-gallo-catechin, epi-catechin-gallerte, epi-gallo-catechin-gallerte and the like.

The low striped bamboo extract can be obtained by extracting low striped bamboo with a low temperature/high pressure extracting method. This method utilizes machine equipment set to a high pressure to allow extraction of low striped bamboo without raising the temperature. The juice thus extracted is then concentrated into the low striped bamboo extract. Low striped bamboo is a species of bamboo grass belonging to the rice plant family and is widely distributed in Japan, china and other countries. The low striped bamboo extract contains triterpenoids ($\beta$-amylene and friedelin) as major ingredients, and sugars such as residual lignin, reduction sugar and glucose. Instead of the low striped bamboo extract, a mixture of synthetic products of these ingredients may be used.

Dokudami (houttuynia herb) is a perennial plant widely distributed in Asia including Japan, Taiwan, China, Himalayan and Java. Like the low striped bamboo extract, the dokudami extract is obtained by the low temperature/high pressure extracting method. The dokudami extract contains quercitrin, afzenin, hyperin, rutin, chlorogenic acid, $\beta$-sitosterol, and cis- & trans-N-(4-hydroxystyryl). Instead of the dokudami extract, a mixture of synthetic products of these ingredients may be used.

Though only one of the extracts of aloe, green tea and dokudami may be used, preferably two or more of them are used in combination, and more preferably all of these extracts are contained in the bactericide of the invention.

Preferable proportions of the aloe extract and like extracts based on 100 $\mu$g of hinokitiol in the composition are: 40 to 300 $\mu$g of the aloe extract, 40 to 300 $\mu$g of the green tea extract, 20 to 50 $\mu$g of the low striped bamboo extract, and 20 to 50 $\mu$g of the dokudami extract. More preferably, all the extracts of aloe, green tea, low striped bamboo and dokudami are contained in the composition used in the invention with the ratio of the total amount of all these extracts to the amount of hinokitiol being 3–3.5:1 (in mass ratio).

The composition (the bactericide against VRE) used in the present invention may further contain at least one of respective extracts of persimmon leaf, pine, cedar, gynostemma pentaphyllum makino, perilla, wasabia, madder, plum, garlic, mint, mugwort, Japanese pepper, rhubarb, thistle, peppermint, loquat, lungwort, lavender, lemon grass and forsythiae fructus, propolis extracted from honey, and the like. These extracts are capable of mitigating the smell and bitter taste peculiar to hinokitiol and improving the solubility of hinokitiol in water without weakening the antibacterial activity of hinokitiol.

The composition used in the present invention contains hinokitiol as an effective component, the aloe extract and like extracts preferably used, other botanical extract components optionally used as required, and a carrier suited for any intended preparation of the bactericide.

The carrier may be any suitable liquid or solid substance as far as it does not lessen the antibacterial activity of hinokitiol. Carrier substances described below may be used alone or as a mixture of two or more of them as required.

Any liquid carrier may be used which can serve as a solvent or a dispersing medium for hinokitiol. Examples of such liquid carriers include water; alcohols such as methanol and ethanol; ketones such as acetone and methyl ethyl ketone; fatty acid esters; aromatic hydrocarbons such as benzene, toluene and xylene; acid amides such as dimethylformamide; and higher fatty acids.

Among them, water is preferably used when the bactericide is used in applications using a great quantity of the bactericide such as spraying or spreading, or in applications for oral administration. Hinokitiol is generally known to have poor solubility in water and can be dissolved up to no more than about 0.2% by mass when used singly. However, by combining hinokitiol with the aloe extract and like extracts it is possible to obtain an aqueous bactericide having a hinokitiol concentration of about 1% by mass. When the composition is used in the form of an aqueous solution, the aqueous solution preferably contains a surface active agent such as glycerin fatty acid ester, and/or a botanical emulsifier such as quillaia saponin, as required. These agents make it possible to provide for an aqueous solution of the bactericide having a hinokitiol concentration of up to 10% by mass.

According to the present invention, a preferable formulation of the composition in the form of the aqueous solution comprises from 0.001% to 10% by mass hinokitiol; from 0.002% to 10% by mass aloe; from 0.002% to 10% by mass green tea; from 0.001% to 5% by mass low striped bamboo; and from 0.001% to 5% by mass dokudami, wherein all percentages are based on the weight of the water, Such an aqueous solution may be prepared by adding 50 $\mu$g to 100 g of hinokitiol, 20 $\mu$g to 100 g of the aloe extract, 20 $\mu$g to 100 g of the green tea extract, and 10 $\mu$g to 50 g of the low striped bamboo extract, and 10 $\mu$g to 50 g of dokudami to 100 g of water. Respective proportions of major components will vary depending on the proportion of hinokitiol relative to water and the presence or absence of any surface active agent.

The composition may be used as medicines to treat a patient infected with VRE, because of the following advantages: (i) the effective component in the composition is hinokitiol having low toxicity, (ii) adding at least one of the aloe extract and like extracts in the composition can reduce the required amount of administration to sterilize VRE.

Where the composition is used as a medicine against VRE, the composition, together with an appropriate carrier, can take various preparation forms such as tablet, pill, powder, solution, suspension, emulsion, granule, capsule, suppository, injection (solution, suspension, etc.), eye wash and ointment.

For example, a tablet may be prepared as containing a vehicle such as lactose, sucrose, sodium chloride, glucose, urea, starch, calcium carbonate, kaolin, crystalline cellulose, or silicic acid; a binder such as water, ethanol, propanol, simple syrup, glucose solution, starch solution, gelatin solution, carboxymethylcellulose, shellac, methylcellulose, potassium phosphate, or polyvinyl pyrrolidone; a disintegrator such as dried starch, sodium alginate, agar powder, laminaran powder, sodium bicarbonate, calcium carbonate, polyoxyethylene sorbitan fatty acid ester, sodium lauryl sulfate, monoglyceride stearate, starch, or lactose; a disintegration inhibitor such as sucrose, stearin, cacao butter, or hydrogenated oil; an absorption promoter such as quaternary ammonium base or sodium lauryl sulfate; a humectant such as glycerin or starch; an adsorbent such as starch, lactose, kaolin, bentonite, or colloidal silicic acid; and a lubricant such as purified talc, stearate, boric acid powder, or polyethylene glycol. As required, such a tablet may take the form of a coated tablet covered with any conventional coating or film such as sugar-coated tablet, gelatin-coated tablet, enteric coated tablet or a film-coated tablet, or a double-layered or multi-layered tablet.

In the case of a pill, it may contain a vehicle such as glucose, lactose, starch, cacao butter, hydrogenated vegetable oil, kaolin, or talc; a binder such as gum arabic powder, tragacanth powder, gelatin, or ethanol; and a disintegrator such as laminaran or agar.

In the case of a suppository, it may contain polyethylene glycol, cacao butter, a higher alcohol, an ester of a higher alcohol, gelatin, a semisynthetic glyceride, and the like.

In the case of a capsule, it may be formed by mixing the effective components with any one of the carriers exemplified above and filling the mixture into a hard or soft gelatin capsule.

Where the composition is used in the form of an injection, any one of the diluents of effective components which are used in the art can be used as a carrier. Examples of such carriers include water, ethyl alcohol, macrogol, propylene glycol, ethoxylated isostearyl alcohol, polyoxylated isostearyl alcohol, and polyoxyethylene sorbitan fatty acid esters. Such an injection may further contain common salt, glucose or glycerin in an amount sufficient to prepare an isotonic solution, and furthermore, a typical solubilizing agent, buffer, soothing agent or the like.

Where the composition is used in the form of an ointment, a wide variety of oleaginous bases known in the art can be used. Examples of specific oleaginous bases include fats and oils such as peanut oil, sesame oil, soybean oil, safflower oil, avocado oil, sunflower oil, corn oil, rapeseed oil, cottonseed oil, castor oil, camellia oil, coconut oil, olive oil, poppy seed oil, cacao oil, beef tallow, lard, and wool fat; mineral oils such as vaseline, paraffin, silicone oil, and squalane; higher fatty acid esters, higher aliphatic alcohols and waxes such as isopropyl myristate, n-butyl miristate, isopropyl linoleate, acetyl ricinoleate, stearyl ricinoleate, diethyl sebacate, diisopropyl adipate, cetyl alcohol, stearyl alcohol, white beeswax, whale wax, and Japan wax; higher fatty acids such as stearic acid, oleic acid, and palmitic acid; and mixtures of mono-, di- or tri-glycerides of saturated or unsaturated fatty acids having 12 to 18 carbon atoms.

In addition to the effective components including hinokitiol and the aloe extract and like extracts, other extracts of persimmon leaf and the like added as required, and the carrier selected depending on the preparation form of the bactericide, the composition may be admixed with appropriate conventional additives such as medically efficacious substances including metallic soap, animal extract, vitamin preparation, hormone preparation and amino acid, dyestuff, dye, pigment, perfume, ultraviolet absorber, humectant, thickening agent, antioxidant, sequestering agent, and pH adjustor.

According to another aspect of the invention, the aqueous composition described above can be administered as disinfection to a site contaminated with VRE, for example a medical site and a food processing site. Where the composition is used for the disinfection of the contaminated site, the composition is preferably formed into a preparation of the spray type adapted to be directly sprayed on medical instruments, floor, wall, ceiling or the like; of the application type adapted for application; or of the impregnation type adapted to impregnate wiping or drying cloth or analogs such as mop, paper towel, wet tissues, and moist hand towel. When the subjects to be sterilized or disinfected are clothes, foods, tableware, gauze, bed sheets, diapers, curtain or the like, the composition is preferably used as added to a detergent, finishing agent or the like.

In the case of preparations of the spray type, application type and impregnation type, the composition for disinfection is preferred in the form of aqueous solution. Liquid carriers such as water, alcohols, esters or higher fatty acids, which serve as solvents or dispersing media of the aforementioned effective components, may be used. Using an alcohol as a liquid carrier can achieve a hinokitiol content in the composition up to about 5% by mass without aloe extract and the like extract. When the water is used as liquid carrier, the preferable composition further contains the aloe extract and the like extracts, because both hinokitiol solubility therein and its antibactrial activity are improved as described above. A higher hinokitiol concentration in such a liquid composition leads to a smaller dose or amount of the composition required.

Where the composition is used by adding to a detergent, finishing agent or the like, there may be used liquid carriers which are compatible with a detergent liquid or solid carriers which are soluble in such a detergent liquid. When used as preparations adapted for spraying, application, impregnation and the like, the aqueous composition may further be diluted with an appropriate solvent or water. The aqueous composition having an increased hinokitiol concentration can advantageously be diluted in these cases.

Where the composition is used as a bactericide against VRE living in intestines of animals such as livestock including bovine, pig, sheep, chicken, turkey and quail, and pets including dog and cat, there are used carriers that are harmless even when eaten, specifically such carriers as used in medicines or the like, preferably water.

When used as such an intestinal bactericide for animals except human, the composition can be readily administered to such animal by feeding the food added with the composition.

EXAMPLES

Preparation of Bactericide Compositions Against VRE

Two compositions shown in Table 1 were prepared.

TABLE 1

| Composition | 1 | 2 |
|---|---|---|
| Purified water | 1000 g | 1000 g |

TABLE 1-continued

| Composition | 1 | 2 |
|---|---|---|
| Hinokitiol | 1 g (0.1%) | 1 g (0.1%) |
| Aloe extract | 1.5 g (0.15%) | — |
| Green tea extract | 1–2 g (0.12%) | — |
| Low striped extract | 0.3 g (0.03%) | — |
| Dokudami extract | 0.3 g (0.03%) | — |

Species of Enterococcus used

The following six species of bacteria were used.
1. *Enterococcus faecalis* KIH-C233 (collected from virginal mucosa of a patient) MIC (μg/ml): VCM2, ABPC1, PCG4, CEZ>32, CMZ>32, EM>32, GM>32, IPM1
2. *Enterococcus faecium* KIH-234 (collected from virginal mucosa of a patient) MIC (μg/ml): VCM0.5, ABPC16, PCG16, CEZ>32, CMZ>32, EM>32, GM>32, IPM1
3. *Enterococcus faecium* KIH-237 (collected from an imported chicken) MIC (μg/ml): VCM500, ABPC4, PCG16, CEZ>32, CMZ>32, EM>32, GM>32, IPM8
4. *Enterococcus gallinarum* KIH-241 (collected from a chicken grown in Japan) MIC (μg/ml): VCM8, ABPC4, PCG1, CEZ>32, CMZ>32, EM>1, GM>32, IPM1
5. *Enterococcus faecalis* standard bacterium IFO-12965
6. *Enterococcus faecium* standard bacterium IFO-3535

It should be noted that the abbreviations "VCM", "ABPC", "PCG", "CEZ", "CMZ", "EM", "GM" and "IPM" used above are indicative of vancomycin, aminobenzylpenicillin, benzylpenicillin, cefazolin, cefmetazole, erythromycin, gentajuycin and imipenem, respectively. Since the concentration of vancomycin in blood can be expected to reach no more than 6 μg/ml at maximum, a minimum inhibitory concentration of 5 μg/ml or more can be said to be an indication of vancomycin resistance. Thus, the bacteria 1 and 2 noted above are vancomycin sensitive, while the bacteria 3 to 6 are vancomycin resistant.

Minimum Inhibitory Concentration of Hinokitiol Against VRE

The minimum inhibitory concentration (MIC) of hinokitiol was determined by the agar plate dilution method.

Diluted solution of the compositions shown in Table 1 was added to a Mueller-Hinton agar medium liquid, and then the mixture liquids were solidified at room temperature to give agar media having respective hinokitiol concentrations of 150 ppm, 100 ppm, 75 ppm, 50 ppm and 25 ppm. These agar media were inoculated with a loopful of each of the above bacteria, followed by incubation at 35° C. for 24 hours. Thereafter, the agar media were examined as to whether a colony grew on each medium or not. The hinokitiol concentration of an agar medium in which no colony grew was determined as a minimum inhibitory concentration. The results are shown in Table 2.

It is to be noted that the incubation at 35° C. for 24 hours is a condition which allows sufficient growth of the bacteria in a culture medium not containing the bactericide at all.

TABLE 2

| Vancomycin resistant Enterococcus | Minimum inhibitory concentration (μg/ml) | |
|---|---|---|
| | Composition 1 | Composition 2 |
| KIHC-233 | 50 | 75 |
| KIHC-234 | 25 | 75 |
| KIHC-237 | 50 | 100 |
| KIHC-241 | 25 | 50 |
| IFO-12965 | 25 | 50 |
| IFO-3535 | 25 | 50 |

As seen from Table 2, the bactericidal compositions of the present invention each exhibited bactericidal activity against any one of the above vancomycin resistant Enterococcus and vancomycin sensitive Enterococcus at a concentration of not more than 100 μg/ml. Further, the composition containing a mixture of extracts of aloe, green tea, low striped bamboo and dokudami in combination with hinokitiol required a lower concentration of hinokitiol than did the composition containing hinokitiol alone. The inventor believes the aloe extract and like extracts enhanced the bactericidal activity of hinokitiol.

Therefore use of at least one of the aloe extract and like extracts in combination with hinokitiol makes it possible to reduce the required amount of hinokitiol. In addition, where the bactericide in the form of an aqueous solution, the solubility of hinokitiol is enhanced and, hence, the administering dose or amount of the aqueous composition can be reduced.

While only certain preferred embodiments of the present invention have been described in detail, as will be apparent for those skilled in the art, certain changes and modifications may be made in embodiment without departing from the scope of the present invention as defined by the following claims.

What is claimed is:

1. A method for killing a vancomycin resistant Enterococcus, which comprises contacting said vancomycin resistant Enterococcus with a composition containing hinokitiol, a metal complex of hinokitiol, a salt of hinokitiol, or a salt of a metal complex of hinokitiol and said composition further contains extracts of aloe, green tea, low striped bamboo and dokudami.

2. The method according to claim 1, wherein the bactericide further contains at least one selected from the group consisting of respective extracts of persimmon leaf, pine, cedar, gynostemma pentaphyllum makino, perilla, wasabia, madder, plum, garlic, mint, mugwort, Japanese pepper, rhubarb, thistle, peppermint, loquat, lungwort, lavender and lemon grass.

3. The method according to claim 1, wherein the bactericide is an aqueous solution containing water as a carrier.

4. The method according to claim 3, wherein the aqueous solution further contains a surface active agent and/or botanical emulsifier.

5. A method of treating an animal infected with vancomycin resistant Enterococcus, which comprises administering an effective amount of a composition containing hinokitiol, a metal complex of hinokitiol, a salt of hinokitiol, or a salt of a metal complex of hinokitiol to said animal infected with said vancomycin resistant Enterococcus to thereby eliminate said vancomycin resistant Enterococcus from said animal with the proviso that said composition further contains extracts of aloe, green tea, low striped bamboo and dokudami.

6. The method according to claim 5, wherein the composition further contains a carrier.

7. A method of disinfecting a site contaminated with a vancomycin resistant Enterococcus, comprising administering an effective amount of a composition containing hinokitiol, a metal complex of hinokitiol, a salt of hinokitiol, or a salt of a metal complex of hinokitiol to a site contaminated with a vancomycin resistant Enterococcus to eliminate said vancomycin resistant Enterococcus from said site with the proviso that said composition further contains extracts of aloe, green tea, low striped bamboo and dokudami.

8. The method according to claim 7, wherein the position further contains water as a carrier.

9. The method according to claim 7, wherein the position further contains alcohol as a carrier.

10. The method according to claim 4, wherein the aqueous solution contains 100 g of water;

from 50 $\mu$g to 100 g of hinokitiol;

from 20 $\mu$g to 100 g of aloe extract;

from 20 $\mu$g to 100 g of green tea extract;

from 10 $\mu$g to 50 g of low striped bamboo; and from 10 $\mu$g to 50 g of dokudami.

* * * * *